United States Patent [19]

Cooper et al.

[11] Patent Number: 5,679,723
[45] Date of Patent: Oct. 21, 1997

[54] HARD TISSUE BONE CEMENTS AND SUBSTITUTES

[75] Inventors: Kevin Cooper, Warren; Chao C. Chen, Edison; Angelo Scopelianos, Whitehouse Station, all of N.J.

[73] Assignee: Ethicon, Inc., Somerville, N.J.

[21] Appl. No.: 710,691

[22] Filed: Sep. 19, 1996

Related U.S. Application Data

[60] Continuation of Ser. No. 416,389, Apr. 6, 1995, abandoned, which is a division of Ser. No. 346,652, Nov. 30, 1994, abandoned.

[51] Int. Cl.$^6$ .............................. A61F 2/02; A61F 2/28; C08G 63/82
[52] U.S. Cl. ..................... 523/115; 424/426; 428/245; 528/358; 623/16
[58] Field of Search .................. 424/426; 428/240, 428/245, 254, 262, 281, 289, 323, 330, 480; 528/354, 355, 358; 623/16; 523/115

[56] References Cited

U.S. PATENT DOCUMENTS

| | | | |
|---|---|---|---|
| 4,373,217 | 2/1983 | Draenert | 3/1.9 |
| 4,636,526 | 1/1987 | Dorman et al. | 521/61 |
| 4,911,953 | 3/1990 | Hosunuma et al. | 427/224 |
| 5,084,051 | 1/1992 | Törmälä et al. | 606/77 |
| 5,108,399 | 4/1992 | Eitenmuller et al. | 106/35 |
| 5,185,408 | 2/1993 | Tang et al. | 525/415 |
| 5,281,265 | 1/1994 | Liu | 106/35 |
| 5,290,494 | 3/1994 | Coombes et al. | 264/41 |
| 5,410,069 | 4/1995 | Nishimura et al. | 548/547 |

*Primary Examiner*—Carlos A. Azpuru
*Attorney, Agent, or Firm*—Emil Richard Skula

[57] ABSTRACT

Absorbable/resorbable mixtures of aliphatic polyesters of poly(lactide), poly(glycolide), poly(trimethylene carbonate), poly(p-dioxanone) and poly($\epsilon$-caprolactone) and calcium containing bone regenerating compounds such as powdered, non-fibrous calcium phosphates are described. The composites when used to manufacture medical devices exhibit improved absorption characteristics and other physical properties.

6 Claims, 1 Drawing Sheet

HARD TISSUE BONE CEMENTS AND SUBSTITUTES

This is a continuation of application Ser. No. 08/416,389, filed Apr. 6, 1995, now abandoned, which is a division of application Ser. No. 08/346,652, filed Nov. 30, 1994, now abandoned.

TECHNICAL FIELD

The field of art to which this invention relates is hard tissue, bone or cartilage, polymer-based cements and substitutes for hard tissue, bone or cartilage. More specifically, biocompatible, absorbable and resorbable mixtures of homo- and co-polymers, as well as blends of polymers, with bone regenerating materials. Especially, homo- and co-polymers and blends of aliphatic polyesters of lactide, glycolide, ε-caprolactone, p-dioxanone, and trimethylene carbonate with auto- or allo-graft bone or cartilage tissues, demineralized bone, or synthetic calcium containing bone regenerating materials such as hydroxyapatite, calcium phosphates, and bioactive glasses (e.g., calcium oxide and other metal oxides).

BACKGROUND OF THE INVENTION

Orthopaedic and plastic surgeons frequently utilize bone substitute materials in surgical procedures to cement or augment hard tissue, e.g., by filling defects. There are many issues involved in the development of a material for cementing or for substituting for hard tissues. A material best suited to this application should be pliable or shapeable and easy to apply. It should also provide a mechanism for hard tissue (bone) ingrowth into the defect site. In addition, a bone substitute implant should be able to withstand the stresses, strains and high compressive forces that bone is subjected to in high load bearing applications (e.g., long bones, spinal column).

Conventional bone substitute materials are available and have been utilized by surgeons as cements and defect fillers. Currently, for example, as described in U.S. Pat. Nos. 5,178,845, 5,281,265, 4,612,053, 5,238,491, pastes or powders consisting of hydroxyapatite (HA), tri- and tetra-calcium phosphate, or harvested bone (auto- or allo-grafts), and an acidic, aqueous liquid (i.e., phosphoric acid, citric acid) carrier are applied to the defect site. After several minutes, the paste hardens, filling the defect site.

Additionally, synthetic bone substitutes can be delivered as preformed, solid, shapeable implants. Harvested bone (allo- or auto-grafts) has also been used for bone substitute applications that require preformed, solid implants. These materials have been shown to be useful in some low-load or non-load bearing applications (e.g., oral-ridge augmentation).

However, several deficiencies are associated with the use of conventional bone substitute materials. For example, bone received from donors (allograft), as with donated blood, has come under suspicion as a possible carrier of infectious agents such as viruses. Surgeons have also become less tolerant to harvesting bone (autograft) from a second site in the patient. Furthermore, the compressive strengths of synthetic bone regenerating materials, due to their brittle ceramic nature, are not high enough to withstand the forces found in medium to high load bearing applications (i.e., orthopedic fractures).

Additionally, U.S. Pat. No. 4,655,777 discloses a biodegradable prosthesis, and a method of producing the biodegradable prosthesis, consisting of a composite composed of a polymer matrix and reinforcing fibers of calcium phosphates. However, use of toxic solvents (DMSO-dimethylene sulfoxide) and polymeric binders (PAN-polyacrylonitrile) to form such reinforcing fibers, may lead to tissue irritation in the final product. Furthermore, the incorporation of dense, highly crystalline reinforcing fibers, of such ceramics, may cause a lack or resorption or very slow resorption rates for the device, leading to poor bone growth at the bony defect site. Additionally, the incorporation of stiff, rigid reinforcing fibers into the polymer matrix, may cause the composite to become difficult to contour, by heating or other methods, for placement into the body site.

Accordingly, there is a need in this art for new bone substitute materials having improved properties. Therefore, to this end, it would be highly desirable to develop novel materials having improved properties when formed into bone cements/substitutes for hard tissue.

Therefore, what is needed in this art are novel absorbable/resorbable polymer/bone regenerating material composites which have improved physical and absorption properties, can be contoured into the defect site, and are easy to apply.

DISCLOSURE OF THE INVENTION

Accordingly, novel, absorbable/resorbable, biocompatible, polymer/bone regenerating material composites are disclosed.

The biocompatible composites include mixtures of:

a) a first absorbable component comprising a polymer formed from aliphatic lactone monomers selected from the group consisting of p-dioxanone, trimethylene carbonate, ε-caprolactone, glycolide, lactide (l, d, dl, meso), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof, and b) a second resorbable component comprising a hard tissue osteoconductive or osteoinductive calcium containing, non-fibrous, powdered compound, wherein the calcium containing compound comprises a material having the formula:

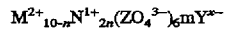

where n=1–10, and m=2 when x=1, and/or m=1 when x=2 where M and N are alkali or alkaline earth metals, preferably calcium, magnesium, sodium, zinc and potassium. $ZO_4$ is an acid radical, where Z is preferably phosphorus, arsenic, vanadium, sulfur or silicon, or is substituted in whole or part with carbonate ($CO_3^{2-}$). Y is an anion, preferably halide, hydroxide, or carbonate.

Another aspect of the present invention is a composite having a first absorbable phase of about 1 weight percent to about 99 weight percent of any of the aliphatic homopolyesters of ε-caprolactone, p-dioxanone, or trimethylene carbonate or copolymers or mixtures thereof, with the remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

Yet a further aspect of the present invention is a composite having a first absorbable phase of about 1 weight percent to about 99 weight percent of aliphatic copolyesters of p-dioxanone or trimethylene carbonate, and glycolide or lactide or mixtures thereof, and in particular, copolymers of p-dioxanone/glycolide, p-dioxanone/lactide, trimethylene carbonate/glycolide and trimethylene carbonate/lactide, with a remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

Further, another aspect of the present invention is a composite having a first absorbable phase of about 1 weight percent to about 99 weight percent of aliphatic copolyesters of $\epsilon$-caprolactone and glycolide or mixtures thereof, or mixtures of homopolymers of $\epsilon$-caprolactone and lactide, with a remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

Preferably, the calcium containing compound used in the composites of the present invention will have a particle size of about 10 microns to about 1000 microns, and most preferably about 100 microns to about 500 microns. The particles are prepared by conventional processes such as pulverizing, milling, and the like.

In yet a further aspect of the present invention, the above described polymers of the present invention may be liquid or low melting, low molecular weight polymers, with or without photocurable groups. The liquid or low melting polymers are of sufficiently low molecular weight, having an inherent viscosity of about 0.05 to about 0.5 dL/g, to yield materials which can easily flow, with or without heat being applied, through a small diameter delivery device such as a syringe, with or without mechanical assistance, a caulking gun, a soft-sided tube, and the like.

Still yet a further aspect of the present invention is a coated biocompatible substrate, such as a surgical mesh comprising a biocompatible, absorbable polyester such as poly(glycolide), poly(lactide), poly($\epsilon$-caprolactone), poly(trimethylene carbonate), poly(p-dioxanone), and combinations thereof, coated with one of the above-described composites of the present invention or a resorbable calcium phosphate or bioactive glass of the present invention in a suitable carrier such as water, saline, water soluble poly(ethylene glycol)s, and combinations thereof.

A further aspect of the present invention is a process by which the composites are prepared. The composites can be prepared by a one-step or a two-step process in which a bone regenerating material is mixed in the reaction vessel with a just-formed polymer (one-step process), or mixed with a pre-formed polymer in a separate vessel (two-step process).

Yet another aspect of the present invention is a biomedical device, especially hard tissue implantable cements or substitutes, comprising the above-described composites.

Yet another aspect of the present invention is a method of conforming a medical device comprised of the composites of the present invention to a body structure. The method entails taking a medical device manufactured from the above-described composites, then conforming it to a body structure through heating or by grinding, shaving, cutting, or otherwise forming or manipulating the device, and then setting it in place in the body structure.

The foregoing and other features and advantages of the present invention will become more apparent from the following description and accompanying examples.

DESCRIPTION OF THE PREFERRED EMBODIMENTS

Figure 1:
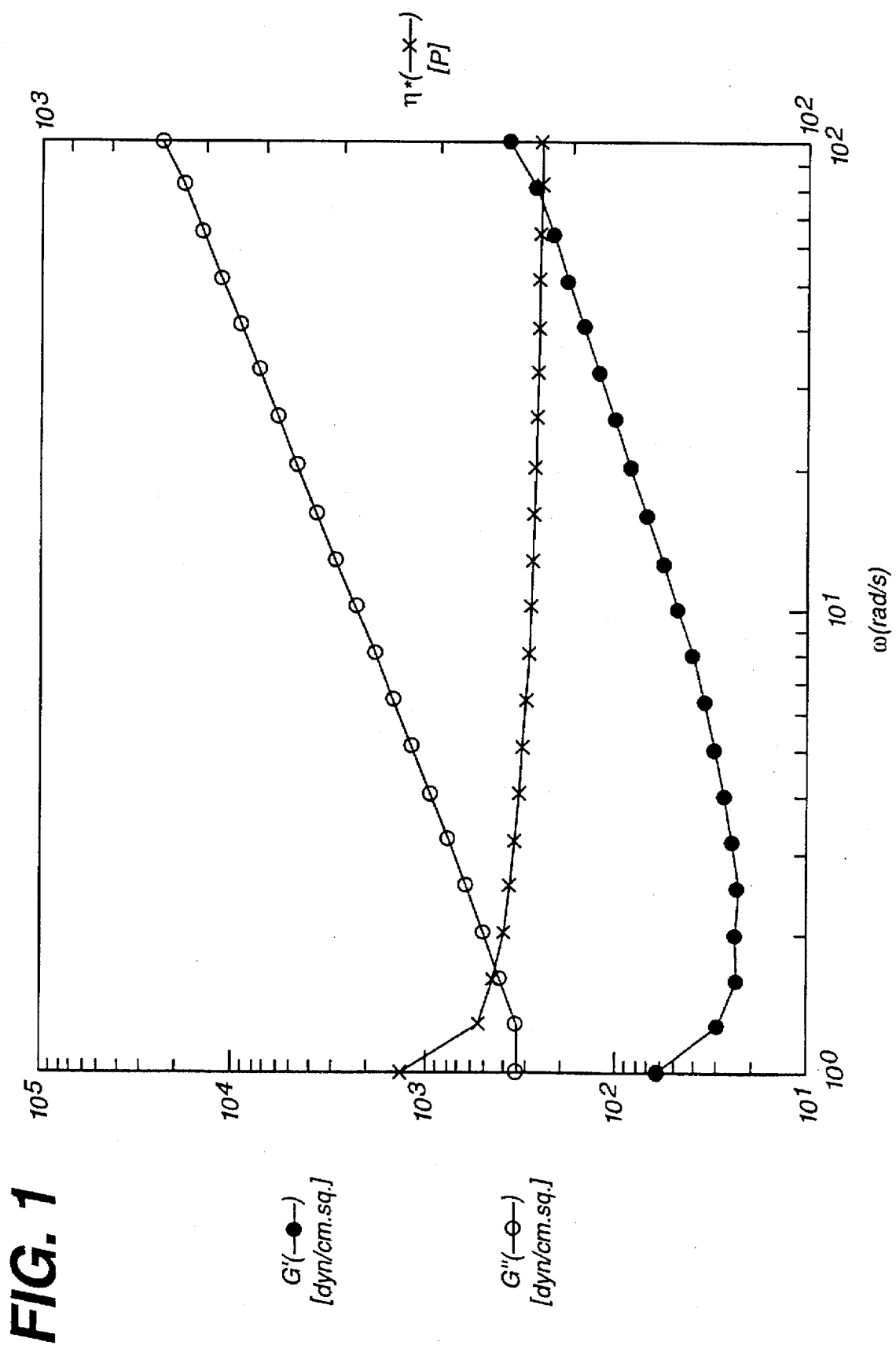
FIG. 1 is a graph of the viscosity as a function of frequency at 37° C. of a composite of the present invention which is a mixture of a 95:5 (mol/mol) poly($\epsilon$-caprolactone-co-trimethylene carbonate) blended with tricalcium phosphate at a blended weight ratio of 25:75.

The aliphatic polyesters useful in the practice of the present invention will typically be synthesized by conventional techniques using conventional processes. For example, in a ring opening polymerization, the lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 220° C., preferably from about 160° C. to about 200° C., until the desired molecular weight and viscosity are achieved.

Under the above described conditions, the homopolymers and copolymers of aliphatic polyesters, will typically have a weight average molecular weight of about 5,000 grams per mole to about 200,000 grams per mole, and more preferably about 10,000 grams per mole to about 100,000 grams per mole. Polymers of these molecular weights exhibit inherent viscosities between about 0.05 to about 3.0 deciliters per gram (dL/g), and more preferably about 0.1 to about 2.5 dL/g as measured in a 0.1 g/dL solution of hexafluoroisopropanol (HFIP) or chloroform at 25° C.

Suitable lactone monomers may be selected from the group consisting of glycolide, lactide (l, d, dl, meso), p-dioxanone, trimethylene carbonate, $\epsilon$-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one and combinations of two or more thereof. Preferred lactone monomers are selected from the group consisting of glycolide, lactide, p-dioxanone, trimethylene carbonate and $\epsilon$-caprolactone.

Most preferably, the aliphatic polyesters consist of homopolymers of poly($\epsilon$-caprolactone), poly(p-dioxanone), or poly(trimethylene carbonate) or copolymers or mixtures thereof, or copolyesters of p-dioxanone or trimethylene carbonate and glycolide or lactide or mixtures thereof, and in particular, copolymers of p-dioxanone/glycolide, p-dioxanone/lactide, trimethylene carbonate/glycolide and trimethylene carbonate/lactide, or copolyesters of $\epsilon$-caprolactone and glycolide or mixtures thereof, or mixtures of homopolymers of $\epsilon$-caprolactone and lactide.

Suitable bone regenerating materials may be selected from the group consisting of auto- or allo-graft bone or cartilage tissues, demineralized bone, or synthetic bone regenerating calcium containing non-fibrous, powdered compounds with the general formula:

$$M^{2+}_{10-n}N^{1+}_{2n}(ZO_4^{3-})_6 mY^{x-}$$

where n=1–10, and m=2 when x=1, or m=1 when x=2 where M and N are alkali or alkaline earth metals, preferably calcium, magnesium, sodium, zinc, and potassium. $ZO_4$ is an acid radical, where Z is preferably phosphorus, arsenic, vanadium, sulfur or silicon, or is substituted in whole or part with carbonate ($CO_3^{2-}$). Y is an anion, preferably halide, hydroxide, or carbonate.

Most preferably, the calcium containing compound comprises mono-, di-, octa-, α-tri-, β-tri-, or tetra-calcium phosphate, hydroxyapatite, fluorapatite, calcium sulfate, calcium fluoride and mixtures thereof.

The calcium containing bone regenerating compound can also contain a bioactive glass comprising metal oxides such as calcium oxide, silicon dioxide, sodium oxide, phosphorus pentoxide, and mixtures thereof, and the like.

The calcium containing compound preferably has a particle size of about 10 microns to about 1000 microns, and more preferably about 100 microns to about 500 microns.

The composites of the present invention will contain sufficient amounts of the absorbable polymer phase and sufficient amounts of the resorbable second bone regenerating phase to effectively function as bone cements or bone substitutes. Typically, the composites will contain about 1 to about 99 weight percent of polymer phase, and more preferably about 5 to about 95 weight percent. The composites will typically contain about 1 to about 99 weight percent of the bone regenerating phase, and more preferably about 5 to about 95 weight percent.

The term "composite" as used herein is defined to mean a material which is comprised of non-fibrous particles or granules, or a non-fibrous powder, of a biocompatible, resorbable, bone regenerating, calcium containing compound of the present invention having a particle size of about 10 to about 1000 microns, in a matrix of a biocompatible, absorbable polyester of the present invention, for use as a bone substitute or a bone cement, and which is resorbable in hard body tissues (bone, cartilage), can be easily contoured to a body structure, possesses good physical properties, and acts as a scaffold for hard tissue (bone) ingrowth.

The term "composite" as used herein is not defined as, and should not be construed as meaning, a material which is comprised of fibers, for reinforcement, e.g., with a high ratio of length to cross sectional area of 10:1 to 1,000,000:1, of a calcium phosphate or bioactive glass, in a matrix of a biocompatible, absorbable polyester for use as a stiff, reinforced fixation device.

The term "bone cement" as used herein is defined to mean a material which adheres to hard tissues such as cartilage and bone in order to fixate fractures and other bony defects and/or fixate fracture fixation devices in cartilage and bone, and to act as a scaffold for bone formation at the cement site. A bone cement should have good adhesive strength and provide a mechanism for bone (hard tissue) ingrowth.

The term "bone substitute" as used herein is defined to mean a material which replaces bone permanently, if non-resorbable, or replaces bone for a period of time until it is resorbed and replaced by the patient's own hard, bony tissues. A bone substitute should be similar in physical and biological properties to the patient's own bone.

It will be appreciated by those skilled in the art that the relative amounts of the first absorbable, polymeric phase to the second resorbable phase in the composites of the present invention will depend upon various parameters including, inter alia, the levels of strength, stiffness, and other physical and thermal properties, absorption and resorption rates, setting and hardening rates, deliverability, etc., which are required. The desired properties of the composites of the present invention and their level of requirement will depend upon the body structure area where the bone cement or substitute is needed. Accordingly, the composites of the present invention will typically contain about 1 weight percent to about 99 weight percent, and more preferably about 5 weight percent to about 95 weight percent of aliphatic polyester homo- or co-polymers, or blends thereof.

The composites of the present invention can be manufactured in the following two-step process. The preformed polymers and bone regenerating materials are individually charged into a conventional mixing vessel having a conventional mixing device mounted therein such as an impeller. Then, the polymers and bone substitutes are mixed at a temperature of about 150° C. to about 220° C., more preferably about 160° C. to about 200° C., for about 5 to about 90 minutes, more preferably for about 10 to about 45 minutes, until a uniformly dispersed composite is obtained. Then, the composite is further processed by removing it from the mixing device, cooling to room temperature, grinding, and drying under pressures below atmospheric at elevated temperatures for a period of time.

In addition to the above manufacturing method, the composites can be prepared by a one-step process by charging the bone regenerating material to a reaction vessel which contains the just-formed polymers. Then, the polymers and bone substitutes are mixed at a temperature of about 150° C. to about 220° C., more preferably about 160° C. to about 200° C., for about 5 to about 90 minutes, more preferably for about 10 to about 45 minutes, until a uniformly dispersed composite is obtained. Then, the composite is further processed by removing it from the mixing vessel, cooling to room temperature, grinding, and drying under pressures below atmospheric at elevated temperatures for a period of time.

Articles such as medical devices may be molded from the composites of the present invention by use of various conventional injection and extrusion processes and molding equipment equipped with dry nitrogen atmospheric chamber(s) at temperatures ranging from about 110° C. to about 230° C., more preferably about 120° C. to about 220° C., with residence times of about 1 to about 10 minutes, more preferably about 2 to about 5 minutes.

The composites of this invention can be melt processed by numerous conventional methods to prepare a vast array of useful devices. These materials can be injection or compression molded to make implantable medical and surgical devices, especially bone regenerating substitutes. The preferred devices include preformed bone defect substitutes, bone waxes, and cartilage replacements.

Additionally, the composites of the present invention which have present low molecular weight polymers that are low melting solids or liquids, and which can be utilized for applications such as injectable bone defect fillers, substitutes, or cements, can be administered to the site by means of conventional delivery devices. The device can be a conventional syringe, with or without mechanical assistance, a caulking-like gun, a soft-sided tube, etc., and the like.

Alternatively, the composites can be extruded to prepare fibers. The filaments thus produced may be spun as multifilament yarn, or meshes, knitted or woven, and formed by conventional molding techniques into reinforced devices and utilized where it is desirable that the structure have high tensile strength and desirable levels of compliance and/or ductility. Useful embodiments include preformed defect bone substitutes, and cartilage replacements for areas where bone or cartilage tissues are damaged or surgically removed.

The composites of the present invention may also be used to coat substrates, such as biocompatible substrates such as meshes, medical devices, etc. The coatings would be made by utilizing liquid composites of the present invention which would then be applied to the substrate by conventional coating techniques such as dipping, spraying, brushing, roller coating, etc. The coating can also be a resorbable calcium phosphate or bioactive glass of the present invention in a suitable carrier such as water, saline, water soluble poly(ethylene glycol)s, and combinations thereof.

Additionally, the composites can be molded to form films which are particularly useful for those applications where a drug delivery matrix in hard tissues (e.g., growth factors) is desired.

Furthermore, the composites of the present invention can be formed into foams, with open or closed cells, which are useful for applications where a high rate of hard tissue ingrowth is required such as in hard tissue replacement areas like the cheek, chin, and vertebrae.

In more detail, the surgical and medical uses of the filaments, films, foams, molded articles, and injectable devices of the present invention include, but are not necessarily limited to osteoinductive or osteoconductive:

a. orthopedic pins, clamps, screws, and plates
b. clips
c. staples
d. hooks, buttons, and snaps
e. preformed bone substitutes
f. injectable bone cements
g. vertebrae discs
h. suture anchors
i. injectable defect fillers
j. preformed defect fillers
k. bone waxes
l. cartilage replacements
m. spinal fixation devices
n. drug delivery devices
o. foams, with open or closed cells, and others.

EXAMPLES

The following examples are illustrative of the principles and practice of this invention, although not limited thereto. Numerous additional embodiments within the scope and spirit of the invention will become apparent to those skilled in the art. The examples describe new composites of aliphatic polyesters and calcium containing, non-fibrous, powdered compounds, preferably calcium phosphates, potentially useful as biomedical devices.

In the synthetic process, the high molecular weight aliphatic polyesters are prepared by a method consisting of reacting lactone monomers via a ring opening polymerization at temperatures of 80° C. to 220° C. for 1 to 24 hours under an inert nitrogen atmosphere until the desired molecular weight and viscosity are achieved.

In the examples, high molecular weight aliphatic polyesters and blends thereof, are prepared and based upon lactone monomers such as glycolide, lactide, p-dioxanone, trimethylene carbonate and ε-caprolactone.

Additionally, post-polymerization reactions to form pendant acrylate groups are performed by a method consisting of reacting hydroxyl pendant side groups of the homo- and co-polymers with acryloyl chloride, or other unsaturated acid halide containing compounds, via esterification at temperatures of 25° C. to 75° C. for 1 to 12 hours under an inert atmosphere.

In the blending process, the composites of the present invention are prepared by either a one or two-step process, in which the bone regenerating material is charged to a reaction vessel containing the just-formed polymer, or by individually charging the synthesized aliphatic homo- and co-polyesters and bone substitutes into a conventional mixing vessel. Then, the polymers and non-fibrous, powdered calcium compounds are mixed at a temperature of 150° C. to 220° C., for 5 to 90 minutes until a uniformly dispersed composite is obtained.

In the examples which follow, the composites, polymers and monomers were characterized for chemical composition and purity (NMR, FT-IR), thermal analysis (DSC), melt rheology (melt stability and viscosity), molecular weight (inherent viscosity), and baseline mechanical properties (Instron stress/strain).

FT-IR was performed on a Nicolet FT-IR. Polymer samples were melt pressed into thin films. Monomers were pressed into KBr pellets. $^1$H NMR was performed on a 300 MHz NMR using $CDCl_3$ or HFAD as a reference.

Thermal analysis of composites, polymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the polymers was also determined by a Rheometrics Dynamic Analyzer RDA II for a period of 1 hour at temperatures ranging from 160° C. to 230° C. under a nitrogen atmosphere.

Inherent viscosities (I.V., dL/g) of the polymers were measured using a 50 bore Cannon-Ubbelhode dilution viscometer immersed in a thermostatically controlled water bath at 25° C. utilizing chloroform or HFIP as the solvent at a concentration of 0.1 dL/g.

Melt viscosity was determined utilizing a Rheometrics Dynamic Analyzer RDA II at temperatures ranging from 160° C. to 230° C. at rate of 1° C./min. to 10° C./min. at frequencies of $1s^{-1}$ to $100s^{-1}$ under a nitrogen atmosphere.

Baseline mechanical properties of cylindrical dumbbells of the composites were performed on an Instron model 1122 at a crosshead rate of 0.35 in/min. Specimen gauge length was 0.35 in., with a width of 0.06 in. Results are an average of 8 to 12 dumbbell specimens.

The cylindrical dumbbells were prepared by utilizing a CSI Mini-max injection molder equipped with a dry nitrogen atmospheric chamber at temperatures ranging from 110° C. to 220° C. with a residence time of 3 minutes.

Several synthetic and composite blending examples will be described in the following few pages. Parts and percentages where used are parts and percentages as specified as weight or moles.

Example 1

Synthesis of a 45:55 (mol/mol) poly(ε-caprolactone-co-glycolide) copolymer

The method described below is similar to those described in U.S. Pat. Nos. 4,643,191, 4,653,497, 5,007,923, 5,047,048, 5,076,807, 5,100,433, and should be known to those skilled in the art.

To a flame dried 500 mL 1-neck round bottom flask equipped with an overhead mechanical stirrer and nitrogen inlet, 51.4 grams (0.45 moles) of ε-caprolactone, 63.8 grams (0.55 moles) of glycolide, 0.13 grams (1.2 moles) of diethylene glycol initiator, and 50.5 microliters of a 0.33M solution of stannous octoate catalyst were added.

The assembly was then placed in a high temperature oil bath at 190° C. The stirred monomers quickly began to melt. The low viscosity melt quickly increased in viscosity. Mechanical stirring of the high viscosity melt was continued for a total reaction time of 24 hours.

The 45:55 (mol/mol) poly(ε-caprolactone-co-glycolide) copolymer was removed from the bath, cooled to room temperature under a stream of nitrogen, isolated and ground. The polymer was then dried under vacuum at 100° C. for 24 hours. Inherent viscosity using HFIP as a solvent was 1.53 dL/g.

Example 2

Blending of a 45:55 (mol/mol) poly(ε-caprolactone-co-glycolide) copolymer with calcium phosphate tribasic at a blended weight ratio of 90:10

115.2 grams of a 45:55 (mol/mol) poly(ε-caprolactone-co-glycolide) copolymer prepared as described in Example 1 was melt blended with 11.5 grams of calcium phosphate tribasic non-fibrous powder at a weight ratio of 90:10 in a Brabender Plasti-corder mixer at a temperature of 190° C. for 23 minutes. The blended composite was removed from the Brabender reactor, cooled, ground and dried under vacuum at 50° C. for 24 hours.

Example 3

Blending of a 45:55 (mol/mol) poly(ε-caprolactone-co-glycolide) copolymer with calcium phosphate tribasic at a blended weight ratio of 80:20

115.2 grams of a 45:55 (mol/mol) poly(ε-caprolactone-co-glycolide) copolymer prepared as described in Example 1 was melt blended with 23 grams of calcium phosphate tribasic non-fibrous powder at a weight ratio of 80:20 in a Brabender Plasti-corder mixer at a temperature of 190° C. for 23 minutes. The blended composite was removed from the Brabender reactor, cooled, ground and dried under vacuum at 50° C. for 24 hours.

Example 4

Synthesis of a 35:65 (mol/mol) poly(ε-caprolactone-co-glycolide) copolymer

The method described below is similar to those described in U.S. Pat. Nos. 4,643,191, 4,653,497, 5,007,923, 5,047,048, 5,076,807, 5,100,433, and should be known to those skilled in the art.

To a flame dried 500 mL 1-neck round bottom flask equipped with an overhead mechanical stirrer and nitrogen inlet, 39.9 grams (0.35 moles) of ε-caprolactone, 75.4 grams (0.65 moles) of glycolide, 0.13 grams (1.2 moles) of diethylene glycol initiator, and 50.5 microliters of a 0.33M solution of stannous octoate catalyst were added.

The assembly was then placed in a high temperature oil bath at 190° C. The stirred monomers quickly began to melt. The low viscosity melt quickly increased slightly in viscosity. Mechanical stirring of the slightly viscous melt was continued for a total reaction time of 24 hours.

The 35:65 (mol/mol) poly(ε-caprolactone-co-glycolide) copolymer was removed from the bath, cooled to room temperature under a stream of nitrogen, and isolated. The polymer was then dried under vacuum at 100° C. for 24 hours. Inherent viscosity using HFIP as a solvent was 1.61 dL/g.

Example 5

Blending of a 35:65 (mol/mol) poly(ε-caprolactone-co-glycolide) copolymer with calcium phosphate tribasic at a blended weight ratio of 90:10

115.3 grams of a 35:65 (mol/mol) poly(ε-caprolactone-co-glycolide) copolymer prepared as described in Example 4 was melt blended with 11.5 grams of calcium phosphate tribasic non-fibrous powder at a weight ratio of 90:10 in a Brabender Plasti-corder mixer at a temperature of 190° C. for 23 minutes. The blended composite was removed from the Brabender reactor, cooled, ground and dried under vacuum at 50° C. for 24 hours.

Example 6

Blending of a 35:65 (mol/mol) poly(ε-caprolactone-co-glycolide) copolymer with calcium phosphate tribasic at a blended weight ratio of 80:20

115.3 grams of a 35:65 (mol/mol) poly(ε-caprolactone-co-glycolide) copolymer prepared as described in Example 4 was melt blended with 23 grams of calcium phosphate tribasic non-fibrous powder at a weight ratio of 80:20 in a Brabender Plasti-corder mixer at a temperature of 190° C. for 23 minutes. The blended composite was removed from the Brabender reactor, cooled, ground and dried under vacuum at 50° C. for 24 hours.

Example 7

Blending of a 35:65 (mol/mol) poly(ε-caprolactone-co-glycolide) copolymer with calcium phosphate tribasic at a blended weight ratio of 50:50

57.7 grams of a 35:65 (mol/mol) poly(ε-caprolactone-co-glycolide) copolymer prepared as described in Example 4 was melt blended with 28.8 grams of calcium phosphate tribasic non-fibrous powder at a weight ratio of 50:50 in a Brabender Plasti-corder mixer at a temperature of 190° C. for 23 minutes. The blended composite was removed from the Brabender reactor, cooled, ground and dried under vacuum at 50° C. for 24 hours.

Example 8

Synthesis of a 25:75 (mol/mol) poly(ε-caprolactone-co-glycolide) copolymer

The method described below is similar to those described in U.S. Pat. Nos. 4,643,191, 4,653,497, 5,007,923, 5,047,048, 5,076,807, 5,100,433, and should be known to those skilled in the art.

To a flame dried 500 mL 1-neck round bottom flask equipped with an overhead mechanical stirrer and nitrogen inlet, 26.2 grams (0.23 moles) of ε-caprolactone, 84.5 grams (0.73 moles) of glycolide, 0.13 grams (1.2 moles) of diethylene glycol initiator, and 48.5 microliters of a 0.33M solution of stannous octoate catalyst were added.

The assembly was then placed in a high temperature oil bath at 190° C. The stirred monomers quickly began to melt. The low viscosity melt quickly increased slightly in viscosity. Mechanical stirring of the slightly viscous melt was continued for a total reaction time of 24 hours.

The 25:75 (mol/mol) poly(ε-caprolactone-co-glycolide) copolymer was removed from the bath, cooled to room temperature under a stream of nitrogen, and isolated. The polymer was then dried under vacuum at 100° C. for 24 hours. Inherent viscosity using HFIP as a solvent was 1.68 dL/g.

Example 9

Blending of a 25:75 (mol/mol) poly(ε-caprolactone-co-glycolide) copolymer with calcium phosphate tribasic at a blended weight ratio of 90:10

110.7 grams of a 25:75 (mol/mol) poly(ε-caprolactone-co-glycolide) copolymer prepared as described in Example 8 was melt blended with 11 grams of calcium phosphate tribasic non-fibrous powder at a weight ratio of 90:10 in a Brabender Plasti-corder mixer at a temperature of 190° C. for 23 minutes. The blended composite was removed from the Brabender reactor, cooled, ground and dried under vacuum at 50° C. for 24 hours.

Example 10

Blending of a 25:75 (mol/mol) poly(ε-caprolactone-co-glycolide) copolymer with calcium phosphate tribasic at a blended weight ratio of 80:20

110.7 grams of a 25:75 (mol/mol) poly(ε-caprolactone-co-glycolide) copolymer prepared as described in Example 8 was melt blended with 23 grams of calcium phosphate tribasic non-fibrous powder at a weight ratio of 80:20 in a Brabender Plasti-corder mixer at a temperature of 190° C. for 23 minutes. The blended composite was removed from the Brabender reactor, cooled, ground and dried under vacuum at 50° C. for 24 hours.

Example 11

Synthesis of a 95:5 (mol/mol) poly(ε-caprolactone-co-trimethylene carbonate) copolymer The method described below is similar to those described in U.S. Pat. Nos. 4,643,191, 4,653,497, 5,007,923, 5,047,048, 5,076,807, 5,100,433, and should be known to those skilled in the art.

To a flame dried 500 mL 1-neck round bottom flask equipped with an overhead mechanical stirrer and nitrogen inlet, 108.4 grams (0.95 moles) of ε-caprolactone, 5.1 grams (0.05 moles) of trimethylene carbonate, 2.94 ml (40 moles) of propylene glycol initiator, and 101 microliters of a 0.33M solution of stannous octoate catalyst were added.

The assembly was then placed in a high temperature oil bath at 160° C. The stirred monomers quickly began to melt. The low viscosity melt increased slightly in viscosity. Mechanical stirring of the slightly viscous melt was continued for a total reaction time of 16 hours.

The 95:5 (mol/mol) poly(ε-caprolactone-co-trimethylene carbonate) copolymer was removed from the bath, cooled to room temperature under a stream of nitrogen, and isolated. The polymer was then dried under vacuum at 80° C. for 24 hours. Inherent viscosity using chloroform as a solvent was 0.15 dL/g.

Example 12

Blending of a 95:5 (mol/mol) poly(ε-caprolactone-co-trimethylene carbonate) copolymer with calcium phosphate tribasic at a blended weight ratio of 25:75

10 grams of a 95:5 (mol/mol) poly(ε-caprolactone-co-trimethylene carbonate) low melt, low I.V. copolymer prepared as described in Example 11 was melt blended with 30 grams of calcium phosphate tribasic non-fibrous powder at a weight ratio of 25:75 in a Brabender Plasti-corder mixer at a temperature of 160° C. for 23 minutes. The blended composite was removed from the Brabender reactor, cooled, ground and dried under vacuum at 50° C. for 24 hours.

Example 13

A bone suture anchor is manufactured from the composite of Example 9 in the following manner. The pelletized polymer/bone regenerating composite material is placed in a hopper which is connected to a conventional melt injection molding machine and heated to above the melting point of the polymer in the mixture (200° C.). The mixture is injected/extruded into a mold, cooled to below the Tg of the polymer (40° C.), which casts a device useful for anchoring soft tissue to hard tissue (bone).

Example 14

A patient is prepared for surgery using conventional preparatory techniques. A chin implant manufactured from the composite of Example 10 is manipulated by heating in order to shape the implant to the patient's mandible (jaw). The implant is then inserted into the patient's jaw and the patient is then closed up in accordance with conventional surgical practices.

The polymer/bone regenerating material composites of the present invention have many advantages over bone regenerating materials of the prior art. For example, in the development of bone substitutes for maxillofacial, oral or orthopedic applications, one of the concerns involves the ability of the device to be manipulated or shaped by the surgeon during surgery to the contours of a body structure.

For example, as found for the high molecular weight aliphatic polyesters/bone regenerating material composites of the present invention, the composites can be manipulated or shaped by various methods such as grinding, heating, cutting, manipulating by hand, etc., by the surgeon during surgery so that the bone substitute follows the contours of a body structure. It is possible to shape these materials, since absorbable, high molecular weight aliphatic polyesters have excellent toughness and strength.

In contrast, bone regenerating ceramic materials (e.g., calcium phosphates, bioactive glasses, etc.) by themselves, have poor toughness and strength, and tend to be very brittle. Consequently, it is very difficult for the surgeon to shape such materials to the contours of a body structure. Therefore, by the combination of powdered calcium phosphates in a matrix of tough, absorbable polyesters, a bone substitute can be formulated which is easy to shape to the contours of a body structure.

In contrast, composites which utilize fibers of calcium phosphates or bioactive glasses may be difficult to shape to a body structure, by heating or other means, due to the increased stiffness caused by the addition of fibrous calcium phosphates.

Additionally, since some surgical applications such as small bony defects found in oral surgery require a material which can be applied as a paste or liquid, then solidify over time in the defect site, an ideal material would be easy to apply and have a setting time which would allow the surgeon time to manipulate the substitute/cement into the defect site.

Low molecular weight aliphatic polyester/bone regenerating material composites of the present invention, can be formulated to meet the requirements of easy application and manipulation into the defect site. Low molecular weight aliphatic polyesters can be varied by molecular weight, composition and monomer type to yield polymers which are viscous liquids or low melting solids (i.e., less than 60° C.) at room temperature. By combining these polymers with bone regenerating materials (i.e., powdered calcium phosphates), composites or dispersions can be formulated which are easy to apply, because of their low viscosities at temperatures slightly above body temperature, and are easy to manipulate into the defect site, due to easy control of solidification by crystallization or crosslinking. This leads to their usefulness as injectable defect fillers.

Previously described bone regenerating materials can also be applied as a low viscosity paste, followed by solidification. However, the pastes can be non-uniform, which can lead to poor bone regeneration. Furthermore, setting times can be difficult to control since setting is determined by the rate of precipitation of the calcium phosphate compounds found in the formulation which is a function of several complicated and contradicting factors, including; the type of calcium phosphate compound(s) used, the setting agent used, the pH of the water phase, and the weight ratio of solid calcium phosphate to liquid phase.

By incorporation of low molecular weight polyesters to a bone regenerating material, a broader range of viscosities for easier application to different types of defect sites, and better, simpler control of setting times, through simple manipulation of the melting point of the polymer, can be obtained (as illustrated by the graph in FIG. 1).

Furthermore, the composites of the present invention can be formulated to yield a bone substitute which will provide a mechanism for hard tissue (bone) ingrowth into the defect site. Composites of the present invention can be prepared where the aliphatic polyester is hydrolyzed so that a porous structure forms. Additionally, since the calcium phosphate is in a powdered, non-fibrous form, fast resorption of the calcium phosphate can occur. This will allow ingrowth of osteoblasts cells and the formation of bone into the defect site.

In contrast, many calcium containing bone regenerating materials can resorb very slowly due to their use of very dense, highly crystalline calcium phosphates, including those composites comprised of dense, crystalline calcium phosphate or bioactive glass fibers. Consequently, their ability to foster hard tissue ingrowth is limited. This leads to poor regeneration of bone in the defect site.

Most importantly, the composites of the present invention have a wide range of physical properties, making them useful as bone and cartilage replacement materials. That is, polymers tend to have excellent compressive strength and fracture toughness. Bioabsorbable polymers can often yield materials which are elastic and ductile with excellent compressive and fracture strength and toughness. Consequently, composites of such polymers with bone regenerating materials of the present invention have good strength and stiffness (See Table).

TABLE STRENGTH OF BONE SUBSTITUTES

| Bone substitute Composition | Wt % CPT* | Yield Strength psi | Modulus psi | Elongation % |
|---|---|---|---|---|
| PCL/PGA 25/75 | 10 | 7000 | 300000 | 5 |

*CPT = CALCIUM PHOSPHATE TRIBASIC

Although this invention has been shown and described with respect to detailed embodiments thereof, it will be understood by those skilled in the art that various changes in form and detail thereof may be made without departing from the spirit and scope of the claimed invention.

We claim:

1. A method of conforming a medical device to a body structure, comprising:

injecting a medical device to effectively conform it to the contours of a body structure, wherein the device comprises:

a liquid, low melt, injectable biocompatible composite, comprising:

a) a first absorbable component comprising a polymer formed from aliphatic lactone monomers selected from the group consisting of p-dioxanone, trimethylene carbonate, ε-caprolactone, delta-valerolactone, beta-butyrolactone, epsilon-decalactone, 2,5-diketomorpholine, pivalolactone, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof wherein said polymer has an inherent viscosity of about 0.05 to about 0.5 dL/g and, b) a second resorbable component comprising a hard tissue osteoconductive or osteoinductive calcium containing compound wherein the calcium containing, non-fibrous, powdered compound is selected from the group consisting of mono-, di-, octa, α-tri-, β-tri, and tetra-calcium phosphate, hydroxyapatite, fluorapatite, calcium sulfate, calcium fluoride, calcium oxide and combinations thereof and, implanting the device in the body structure.

2. A method of delivering a medical device to a body structure, comprising:

loading a liquid, low melt, injectable biocompatible composite into a delivery device, the composite comprising:

a) a first absorbable phase comprising a polymer formed from aliphatic lactone monomers selected from the group consisting of p-dioxanone, trimethylene carbonate, ε-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and copolymers, and blends thereof, wherein said polymer has an inherent viscosity of about 0.05 to about 0.5 dL/g, and b) a second resorbable phase comprising a hard tissue osteoconductive or osteoinductive calcium containing, non-fibrous, powdered compound selected from the group consisting of mono-, di, octa, α-tri, β-tri, and tetra-calcium phosphate, hydroxyapatite, fluorapatite, calcium sulfate, calcium fluoride, calcium oxide and combinations thereof, wherein the calcium containing compound has a particle size of about 100 microns to 500 microns and wherein the composite contains about 10 wt. % to about 50 wt. % of the second resorbable phase; and injecting the composite to a body structure, wherein the polymer of the composite of claim 1 has an inherent viscosity of about 0.05 to about 0.5 dL/g, such that the composite can easily flow, with or without the application of heat, through the delivery device to a body structure.

3. A method of conforming a medical device to a body structure, comprising:

injecting a medical device to effectively conform it to the contours of a body structure, wherein the device comprises:

a liquid, low melt, injectable biocompatible composite, comprising:

a) a first absorbable component comprising a polymer selected from the group consisting of poly(p- dioxanone-co-glycolide), poly(trimethylene carbonate-co-glycolide), poly(ε-caprolactone-co-glycolide), poly(p-dioxanone-co-lactide), and poly(trimethylene carbonate-co-lactide), and combinations thereof, and wherein said polymer has an inherent viscosity of about 0.05 dL/g to about 0.5 dL/g, and b) a second resorbable component comprising a hard tissue osteoconductive or osteoinductive calcium containing compound wherein the calcium containing, non-fibrous, powdered compound selected from the group consisting of mono-, di-, octa, α-tri-, β-tri, and tetra-calcium phosphate, hydroxyapatite, fluorapatite, calcium sulfate, calcium fluoride, calcium oxide and combinations thereof and, implanting the device in a body structure.

4. A method of conforming a medical device to a body structure, comprising:

injecting a medical device to effectively conform it to the contours of a body structure, wherein the device comprises:

a liquid, low melt, injectable biocompatible composite, comprising:

a) a first absorbable phase comprising a polymer selected from the group consisting of poly(p-dioxanone-co-glycolide), poly(trimethylene carbonate-co-glycolide), poly(ε-caprolactone-co-glycolide), poly(p-dioxanone-co-lactide), and poly(trimethylene carbonate-co-lactide), and blends thereof, and wherein said polymer has an inherent viscosity of about 0.05 dL/g to about 0.5 dL/g, and b) a second resorbable phase comprising a hard tissue osteoconductive or osteoinductive calcium containing compound wherein the calcium containing, non-fibrous, powdered compound selected from the group consisting of mono-, di-, octa, α-tri-, β-tri, and tetra-calcium phosphate, hydroxyapatite, fluorapatite, calcium sulfate, calcium fluoride, calcium oxide and combinations thereof.

5. A method of conforming a medical device to a body structure, comprising:

injecting a medical device to effectively conform it to the contours of a body structure, wherein the device comprises:

a liquid, low melt biocompatible composite, comprising:

a) a first absorbable component comprising a mixture of homopolymers selected from the group consisting of poly(p-dioxanone), poly(trimethylene carbonate), poly(ε-caprolactone) and poly(glycolide), and combinations thereof, and wherein said polymer has an inherent viscosity of about 0.05 dL/g to about 0.5 dL/g, and b) a second resorbable component comprising a hard tissue osteoconductive or osteoinductive calcium containing compound wherein the calcium containing, non-fibrous, powdered compound selected from the group consisting of mono-, di-, octa, α-tri-, β-tri, and tetra-calcium phosphate, hydroxyapatite, fluorapatite, calcium sulfate, calcium fluoride, calcium oxide and combinations thereof and, implanting the device in the body structure.

6. A method of conforming a medical device to a body structure, comprising:

injecting a medical device to effectively conform it to the contours of a body structure, wherein the device comprises:

a liquid, low melt, injectable biocompatible composite, comprising:

a) a first absorbable component comprising a mixture of homopolymers selected from the group consisting of poly(p-dioxanone), poly(trimethylene carbonate), poly(ε-caprolactone) and poly(lactide), and combinations thereof, and wherein said polymer has an inherent viscosity of about 0.05 dL/g to about 0.5 dL/g, and b) a second resorbable component comprising a hard tissue osteoconductive or osteoinductive calcium containing compound wherein the calcium containing, non-fibrous, powdered compound selected from the group consisting of mono-, di-, octa, α-tri-, β-tri, and tetra-calcium phosphate, hydroxyapatite, fluorapatite, calcium sulfate, calcium fluoride, calcium oxide and combinations thereof and, implanting the device in the body structure.

\* \* \* \* \*